United States Patent
Suga et al.

(10) Patent No.: US 6,539,555 B2
(45) Date of Patent: Apr. 1, 2003

(54) SANITARY PANTY

(75) Inventors: Ayami Suga, Kagawa (JP); Mitsuhiro Wada, Kagawa (JP)

(73) Assignee: Uni-Charm Corporation, Kawanoe (JP)

(*) Notice: Subject to any disclaimer, the term of this patent is extended or adjusted under 35 U.S.C. 154(b) by 0 days.

(21) Appl. No.: 09/812,796

(22) Filed: Mar. 20, 2001

(65) Prior Publication Data
US 2001/0025386 A1 Oct. 4, 2001

(30) Foreign Application Priority Data
Mar. 31, 2000 (JP) ........................................ 2000-096859

(51) Int. Cl.⁷ .............................. A41B 9/02; A61F 13/15
(52) U.S. Cl. ............................ 2/406; 2/400; 604/385.2
(58) Field of Search ............................ 2/400, 402, 403, 2/406, 401, 228, 238; 604/385.1–402

(56) References Cited

U.S. PATENT DOCUMENTS

| | | | | |
|---|---|---|---|---|
| 2,616,427 A | * | 11/1952 | Pettit | 604/385.1 |
| 3,687,141 A | * | 8/1972 | Matsuda | 604/385.1 |
| RE28,483 E | * | 7/1975 | Ralph | 604/385.1 |
| 4,355,425 A | * | 10/1982 | Jones et al. | 2/402 |
| 4,892,536 A | * | 1/1990 | DesMarais et al. | 604/385.2 |
| 5,855,573 A | * | 1/1999 | Johansson | 604/385.2 |
| 5,940,887 A | * | 8/1999 | Rajala et al. | 2/400 |

FOREIGN PATENT DOCUMENTS

| | | | |
|---|---|---|---|
| FR | 2368907 | 5/1978 | A41B/13/04 |
| GB | 2282053 | 3/1995 | A61F/13/72 |
| JP | 07-136214 | 5/1995 | |

OTHER PUBLICATIONS

Australian Search Report.

* cited by examiner

Primary Examiner—Gloria M. Hale
(74) Attorney, Agent, or Firm—Darby & Darby

(57) ABSTRACT

Provided is a sanitary panty including a panty body formed with a front part, a back part and a crotch part located between the front part and the back part; and a support member. The panty body has a waist portion formed with an upper edge portion of the front part and an upper edge portion of the back part, and a pair of leg openings. The support member is provided inside of the panty body and has elastic stretchability in a longitudinal direction extending from the front part to the back part. The support member is fitted at both ends only with the front and back parts of the panty body. The support member has a narrower width portion of which the width is in a range of 20 to 40 mm and extending from the crotch part to the back part. The width of the support member gradually increases from a terminal end of the narrower width portion in the back part to the waist portion thereof.

8 Claims, 3 Drawing Sheets

SANITARY PANTY

BACKGROUND OF THE INVENTION

1. Field of the Invention

The present invention relates generally to a sanitary panty which has a superior wearability and a greater level of comfort when worn. More particularly, the invention relates to a sanitary panty which can tightly fit a sanitary napkin fitted on a crotch part by deforming the sanitary napkin into a generally reverse V-shaped cross-section (i.e., a convex form).

2. Description of the Related Art

A sanitary panty typically has a structure, in which a waterproof sheet is sewn on the inside of a crotch cloth portion of a normal lady's panty for preventing leakage and the external extrusion of menstrual blood. On the other hand, measures have also been taken such that a cloth for fitting the sanitary napkin is provided on the inside of the sanitary panty.

In Japanese Unexamined Patent Publication (Kokai) No. Heisei 7-136214, there is disclosed a sanitary panty that is provided for preventing leakage and the external extrusion of menstrual blood. FIG. 3 is a development elevation showing a typical sanitary panty among those disclosed in the above-identified publication.

The sanitary panty illustrated in FIG. 3 is formed with a front part 1, a back part 2 and a crotch part 3. A side edge 1a of the front part 1 and a side edge 2a of the back part 2 are joined and a side edge 1b of the front part 1 and a side edge 2b of the back part 2 are joined to form a panty with a waist portion 5 and leg openings 4.

On the other hand, a napkin fitting crotch cloth 10 is provided inside of the crotch part 3. The napkin fitting crotch cloth 10 is formed with a crotch cloth strip 6 having a width smaller than that of the crotch part 3 and a pair of elastic strips 7 and 8 fixed on both side portions of the crotch cloth strip 6. The crotch cloth strip 6 is joined with the waist portion 5 together with the elastic strips 7 and 8, in the front part 1. Also, the crotch cloth strip 6 extends to an intermediate position of the back part 2. From the terminating end of the crotch cloth strip 6, the elastic strips 7 and 8 extend to be joined with the waist portion 5 in the back part 2.

Particularly, when a sanitary napkin with flaps is fitted, the flaps are turned back for enwrapping both side edge portions of the crotch cloth strip 6 of the napkin fitting crotch cloth 10.

In the conventional sanitary panty, the width of the napkin fitting crotch cloth 10 is relatively wide, 30 to 70 mm. Furthermore, from the terminal end of the crotch part 3, the elastic strips 7 and 8 extend further to reach the waist portion 5 with a gradually increasing distance therebetween. Accordingly, the sanitary napkin fitted on the crotch cloth strip 6 will not penetrate into a rump-cleft. Also, by the elastic strips 7 and 8 provided on both sides of the napkin fitting crotch cloth 10, both side portions of the napkin are urged toward the wearer's body. The napkin is not deformed into substantially reverse V-shaped cross-section adapting to the crotch part of the wearer's body. As a result, the sanitary napkin cannot be tightly fitted to the crotch part of the wearer's body to easily cause side leakage of body fluid.

On the other hand, in cases where the sanitary napkin is set by sticking an adhesive layer formed on the outer surface of a back sheet of the sanitary napkin, since the elastic contracting force of the elastic strips 7 and 8 acts on the crotch cloth strip 6, the crotch cloth strip 6 may be contracted relative to the sanitary napkin to possibly cause peeling off to cause disposition of the napkin while it is worn.

SUMMARY OF THE INVENTION

Therefore, it is an object of the present invention to provide a sanitary panty which can easily urge a center portion of a sanitary napkin for tightly fitting the latter onto a wearer's body as worn on a crotch part, and can prevent disposition of the sanitary napkin relative to the panty.

According to an aspect of the invention, a sanitary panty may comprise:

a panty body formed with a front part, a back part and a crotch part located between the front part and the back part, the panty body having a waist portion formed with an upper edge portion of the front part and an upper edge portion of the back part, and a pair of leg openings; and a support member provided inside of the panty body and having elastic stretchability in a longitudinal direction extending from the front part to the back part, the support member being fitted at both ends only with the front and back parts of the panty body, the support member having a narrower width portion of which width is in a range of 20 to 40 mm and extending from the crotch part to the back part, and the width of the support member gradually increasing from a terminal end of the narrower width portion in the back part to the waist portion of the back part.

In the sanitary panty according to the present invention, the narrower width portion of the support member can be tightly or firmly fitted on the crotch part (perineal region) and rump-cleft to easily fit a sanitary napkin to the crotch part of wearer's body. Also, since the narrower width portion of the support member is smaller than the width of the sanitary napkin, the sanitary napkin is pulled upwardly in the crotch part to be a substantially reverse V-shaped cross-section. Thus, the sanitary napkin can be tightly fitted on the crotch part of the wearer's body.

On the other hand, in the back part, both side edges of the support member are preferably both inwardly curved shape.

With such a shape, the narrower width portion of the support member easily penetrates into a woman's rump-cleft.

The support member is preferably formed with a non-stretchable cloth located at the crotch part, and stretchable clothes connected to both ends of the non-stretchable cloth.

When the non-stretchable cloth is used in the crotch part, the adhesive layer on the outer surface of the back sheet of the sanitary napkin is hardly peeled from the support member to enhance sanitary napkin from mispositioning.

The panty body may be formed with a non-stretchable material having a maximum distortion that is less than or equal to 10%. When the panty body is non-stretchable, the center portion of the napkin is urged to the wearer's body by the stretchability of the support member.

Both end portions of the support member may be joined with the waist portion of the front part and the back part of the panty body. In a free condition where no stretching force is applied, a length of the support member in the longitudinal direction is in a range of 70 to 90% with respect to a length of the panty body in the longitudinal direction.

An elastic modulus in the longitudinal direction of a stretchable material forming the support member may be in a range of 30 to 70 mN.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of a sanitary panty of the present invention with reference to the accompanying drawings. In the following description, numerous specific details are set forth in order to provide a through understanding of the present invention. It will be obvious, however, to those skilled in the art that the present invention may be practiced without these specific details. In other instances, well-known structures are not shown in detail in order to avoid unnecessary obscurity of the present invention.

Figure 1:
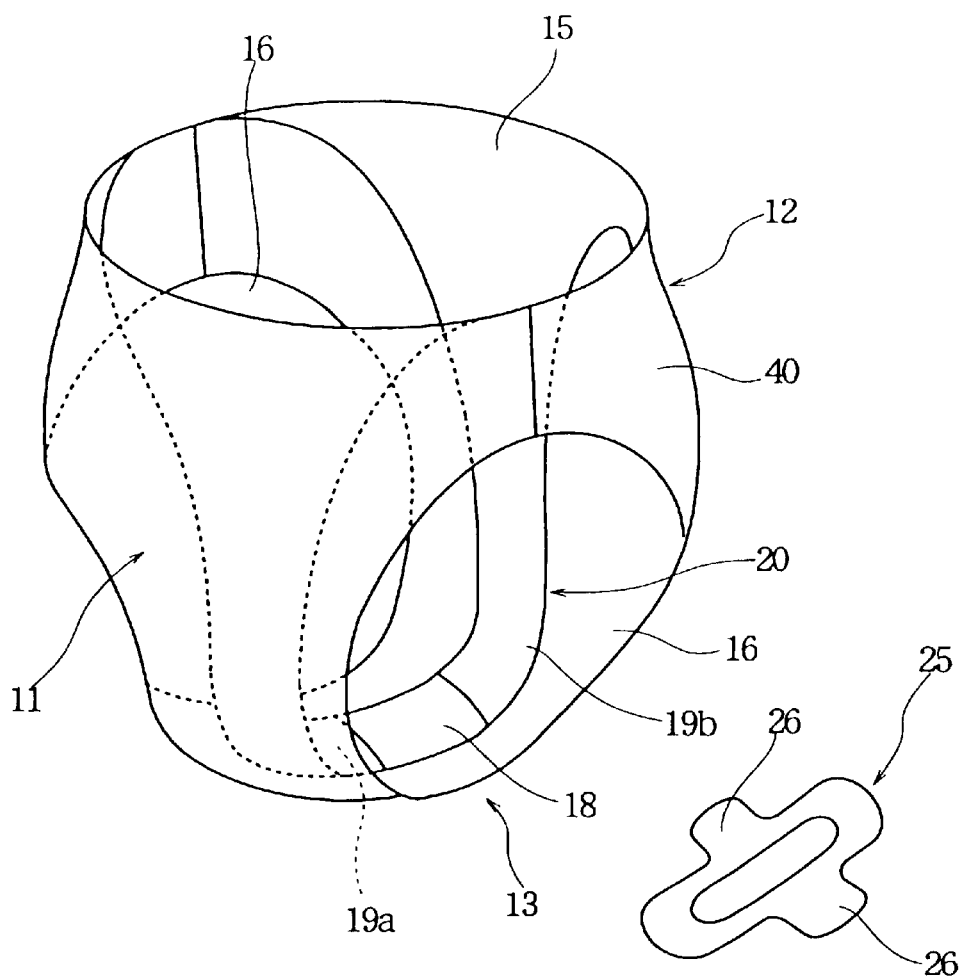
FIG. 1 is a perspective view showing the preferred embodiment of a sanitary panty according to the present invention.
Figure 2:
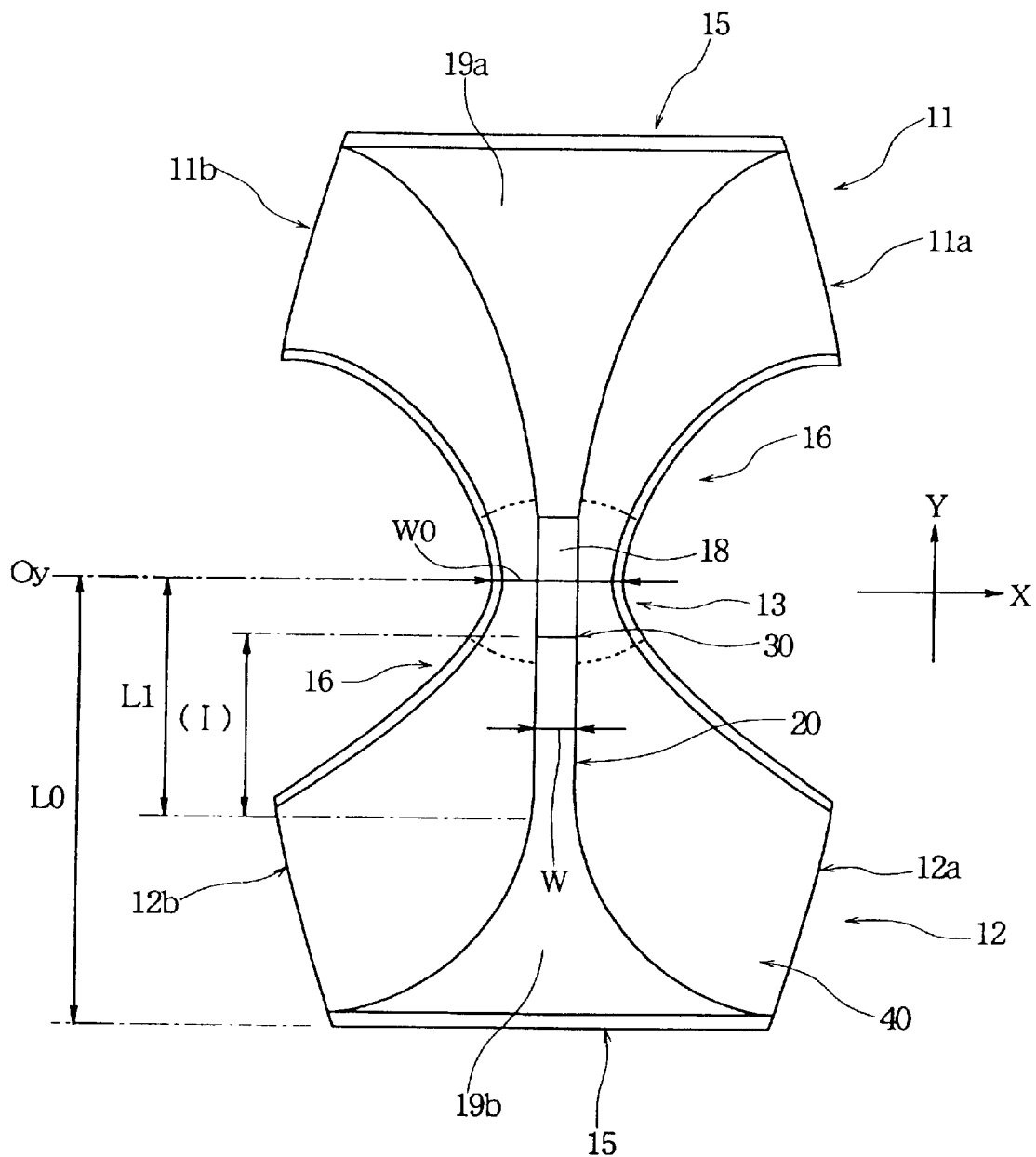
FIG. 2 is a development elevation of the sanitary panty of FIG. 1.
Figure 3:
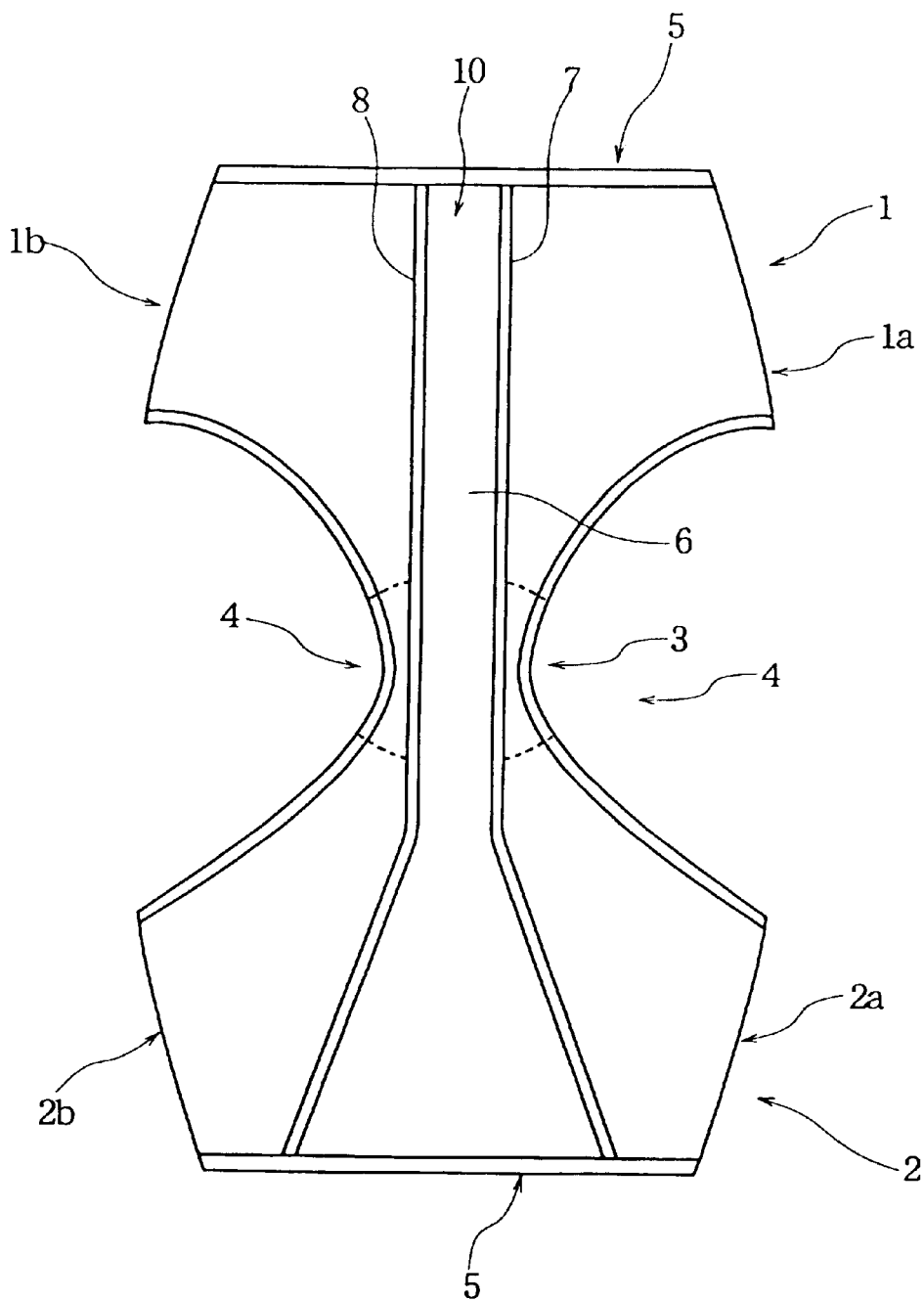
FIG. 3 is a development elevation of the conventional sanitary panty.

FIG. 1 is a perspective view of the preferred embodiment of a sanitary panty according to the present invention, and FIG. 2 is a development elevation thereof. In FIG. 1, the Y direction, along which a front part 11, a crotch part 13 and a back part 12 are continued, will be hereinafter referred to as a longitudinal direction, and the X direction perpendicular to the Y direction will be hereinafter referred to as a latitudinal direction.

The shown sanitary panty includes a panty body 40 constituted of the front part 11, the back part 12 and the crotch part 13. A side edge 11a of the front part 11 and a side edge 12a of the back part 12 are joined and a side edge 11b of the front part 11 and a side edge 12b of the back part 12 are joined to form the panty body 40 with a waist portion 15 and leg openings 16.

A support member 20 is provided inside of the panty body 40. The support member 20 extends over the front part 11, the crotch part 13 and the back part 12 in the longitudinal direction. One of opposite ends in the longitudinal direction is fixed to the waist portion 15 of the front part 11 of the panty body 40, and the other end is fixed to the waist portion 15 of the back part 12 of the panty body 40 ("opposite ends in the longitudinal direction" are also referred to as end edge portions). The support member 20 is not joined or sewn other than the waist portion 15. Namely, an intermediate portion of the support member 20 is not fitted to the panty body.

The support member 20 is formed with a stretchable member 19b formed with a stretchable material gradually narrowed in width from the waist portion 15 to the crotch portion 13 in the back part 12, a stretchable member 19a formed with a stretchable member material gradually narrowed in width from the waist portion 15 to the crotch part 13 in the front part 11, and a non-stretchable member 18 joined between both stretchable members 19a and 19b. As shown in FIG. 1, when the sanitary panty is formed into a three-dimensional shape approximated with the condition worn on a wearer's body, the non-stretchable member 18 is located at a position overlapping with the inside of the crotch part 13 of the panty body 40.

As set forth above, since the shown embodiment of the sanitary panty according to the invention is provided with the non-stretchable member 18 at a central portion of the support member 20 in longitudinal direction and the non-stretchable member 18 is elastically suspended by the stretchable members 19a and 19b at both sides in the longitudinal direction, the non-stretchable member 18 can move freely relative to the crotch part 13 of the panty body 40. On the other hand, the non-stretchable member 18 is positioned in the crotch part 13 which serves as a napkin application zone. To the non-stretchable member 18, a longitudinal tension force is applied by the stretchable members 19a and 19b. Therefore, when an adhesive layer provided on the outer surface of the back sheet of the sanitary napkin 25 is stuck on the non-stretchable member 18, the crease will never be formed in the non-stretchable member 18 to hardly cause peeling of the stuck portion by the adhesive layer, and to hardly cause mispositioning of the sanitary napkin 25 in the crotch part.

When the sanitary panty is worn, the support member 20 acts to pull up the center portion of the sanitary napkin 25 applied to the crotch portion 13 so that the sanitary napkin 25 is deformed into substantially reverse V-shaped cross-section (i.e., a convex form). The support member 20 may also tightly fit even in the rump-cleft with urging the sanitary napkin 25 to penetrate the deformed reverse V-shaped portion of the sanitary napkin into the rump-cleft.

Accordingly, when the sanitary napkin 25 is applied with turning back wings 26 extending from both sides thereof for enwrapping both side edge portions (edge portions of the leg openings) of the crotch part 13 of the panty body 40, the sanitary napkin 25 is deformed into substantially reverse V-shaped cross-section so that the center portion of the napkin can be tightly fitted to the wearer's body. On the other hand, when a sanitary napkin without the wings 26 is applied, the center portion of the napkin is urged to the wearer's body by the non-stretchable member 18 of the support member 20 to easily deform into substantially reverse V-shaped cross-section toward the wearer's body.

As set forth above, so that the sanitary napkin is deformed into a substantially reverse V-shaped cross-section from the crotch part of the wearer's body to the rump-cleft to facilitate tight fitting, a width W of the support member 20 located in the crotch part 13 becomes smaller than the width of the sanitary napkin. This narrower width portion is continued to the back part 12. Both side edge portions of the support member 20 are arc-shaped and arranged in a back-to-back relationship, i.e, an inwardly curved shape to gradually increase the width from the narrower width portion to the waist portion 15.

As shown in FIG. 2, in the support member 20, the width W of the narrower width portion which is constituted of the non-stretchable member 18, and that of the stretchable member 19b in a region (I) extending from a joining portion 30 with the non-stretchable member 18 to the intermediate portion in the back part 12, are in a range of 20 to 40 mm. The width W is selected to be less than or equal to two third of the width of the sanitary napkin, and more preferably less than or equal to one half. On the other hand, the width W0 in the crotch part 13 of the panty body 40 is selected to be substantially equal to or slightly wider than the width of the sanitary napkin. Therefore, the width W0 is in a range of 60 to 80 mm.

In order to deform the sanitary napkin into the substantially reverse V-shaped cross-section by elastic force of the support member 20 to tightly fitting in into the crotch part and rump-cleft of the wearer's body, the width W of the narrower width portion of the support member 20 is preferably less than or equal to two thirds of the width W0 of the crotch part 13 of the panty body 40, and further preferably less than or equal to one half.

The widths W and W0 are necessary dimensions for stably applying the sanitary napkin 25 with the wings 26 shown in FIG. 1. The width of a napkin body of the typical sanitary napkin is 40 to 70 mm.

As shown in FIG. 2, when the sanitary panty is developed with orienting Y direction in the longitudinal direction and assuming that the length from the longitudinal center Oy to the waist portion 15 of the back part 12 is L0, a length from the longitudinal center Oy to the terminal end of the boundary region (I) of the back part 12, namely the length L1 of the narrower width portion of the width W of the support member 20 is preferably less than or equal to four fifth of the length L0 and larger than or equal to one fourth of the length L0. Further preferably, the length L1 is larger than or equal to one half thereof. Therefore, when the sanitary panty is worn, the narrower width portion in the region I of the support member 20 easily penetrates into the rump-cleft.

The material forming the panty body 40 is preferably a non-stretchable material. Normally, a woven fabric is used and the maximum distortion when being forcedly stretched in each direction is less than or equal to 10%.

On the other hand, the stretchable material forming the stretchable members 19*a* and 19*b* of the support member 20 is a woven fabric formed with an elastically stretchable fiber or a woven fabric inweaved elastically stretchable fiber. For example, the stretchable material consists of nylon fiber (non-stretchable fiber) and polyurethane fiber (stretchable fiber). An elastic modulus of the stretchable material in the longitudinal direction is preferred to be 30 to 70 mN. The elastic modulus is a ratio (contracting force acting entirely/distortion) upon stretching the entire support member 20 shown in FIG. 2 in the longitudinal direction (Y direction). The non-stretchable member 18 is a woven fabric formed with non-stretchable fiber, such as nylon.

From the above, when the sanitary panty is worn or is formed into a three-dimensional shape similar to the shape where it is worn, the support member 20 is placed into a condition of being stretched in the longitudinal direction. Then, the contraction stress of the support member 20 becomes larger than the contraction stress of the panty body 40.

Accordingly, the sanitary napkin applied to the crotch part 13 is deformed into the substantially reverse V-shaped cross-section so that the sanitary napkin is tightly fitted to the crotch part and rump-cleft of the wearer's body by the narrower width portion of the support member 20.

On the other hand, since the panty body 40 and the support member 20 are sewn only in the waist portion 15, disposition of the panty which can be caused by motion of wearer's body may not influence the support member 20. Therefore, the sanitary napkin may be firmly fitted on the wearer's body while maintaining the substantially reverse V-shaped cross-section so as not to form a gap therebetween, thereby preventing leakage of menstrual blood.

Furthermore, since sufficient napkin urging effect can be obtained only by the support member 20, the panty body 40 may be formed with a material having a low stretchability. A material having substantially high air permeability, low density and thin material may be used. Therefore, unnecessary oppressive feeling or odors can be eliminated to provide the panty with superior comfort when it is worn.

As set forth above, in the sanitary panty according to the present invention, the support member is provided so that mispositioning of the panty which can be caused by motion of wearer's body may not influence the napkin fitting portion. Therefore, the sanitary napkin may be firmly fitted into the rump-cleft of the wearer's body with maintaining substantially reverse V-shaped cross-section. Even when the wearer moves the body, the sanitary napkin may not cause mispositioning in the longitudinal and lateral directions.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. A sanitary panty comprising:
    a panty body formed with a front part, a back part and a crotch part located between said front part and said back part, said panty body having a waist portion formed with an upper edge portion of said front part and an upper edge portion of said back part, and a pair of leg openings; and
    a support member provided inside of said panty body and having elastic stretchability in a longitudinal direction extending from said front part to said back part, said support member being fitted at both ends only with said front and back parts of said panty body,
    said support member formed separately from said panty body having a narrower width portion of which width is in a range of 20 to 40 mm and extending from said crotch part to said back part, and the width of said support member gradually increasing from a terminal end of sid narrower width portion in said back part to said waist portion of said back part.

2. A sanitary panty as set forth in claim 1, wherein in said back part, both side edges of said support member are both inwardly curved shape.

3. A sanitary panty as set forth in claim 1, wherein said support member is formed with a non-stretchable cloth located at said crotch part, and stretchable cloth's connected to both ends of said non-stretchable cloth.

4. A sanitary panty as set forth in claim 1, wherein said panty body is formed with a non-stretchable material having the maximum distortion less than or equal to 10%.

5. A sanitary panty as set forth in claim 1, wherein both end portions of said support member are joined with said waist portion of said front part and said back part of said panty body, and in a free condition where no stretching force is applied, a length of said support member in the longitudinal direction is in a range of 70 to 90% with respect to a length of said panty body in the longitudinal direction.

6. A sanitary panty as set forth in claim 1, wherein an elastic modulus in the longitudinal direction of a stretchable material forming said support member is in a range of 30 to 70 mN.

7. A sanitary panty comprising:
    a panty body formed with a front part, a back part and a crotch part located between said front part and said back part, said panty body formed of a non-stretchable material having a maximum distortion less than or equal to 10%, and having a waist portion formed with an upper edge portion of said front part and an upper edge portion of said back part, and a pair of leg openings; and a support member provided inside of said panty body and having elastic stretchability in a longitudinal direction extending from said front part to said back part, said support member being fitted at both ends only with said front and back parts of said panty body, said support member formed having a narrower width portion of which width is in a range of 20 to 40 mm and extending from said crotch part to said back part, and the width of said support member gradually increasing from a terminal end of said narrower width portion in said back part to said waist portion of said back part.

8. A sanitary panty comprising:

a panty body formed with a front part, a back part and a crotch part located between said front part and said back part, said panty body having a waist portion formed with an upper edge portion of said front part and an upper edge portion of said back part, and a pair of leg openings; and a support member provided inside of said panty body and having elastic stretchability in a longitudinal direction extending from said front part to said back part, said support member being fitted at both ends only with said front and back parts of said panty body, said support member having a narrower width portion of which width is in a range of 20 to 40 mm and extending from said crotch part to said back part, and the width of said support member gradually increasing from a terminal end of said narrower width portion in said back part to said waist portion of said back part;

wherein an elastic modulus in a longitudinal direction of a stretchable material forming said support member is in a range of 30 to 70 mN.

* * * * *